United States Patent [19]
Arya et al.

[11] Patent Number: 5,770,736
[45] Date of Patent: Jun. 23, 1998

[54] REAGENTS FOR CLEAVAGE OR CROSSLINKING OF BIOMOLECULES USING NONDIFFUSIBLE REACTIVE INTERMEDIATES

[75] Inventors: Dev P. Arya, Boston; Theresa Ann Devlin, Jamaica Plain; David Jebaratnam, Lexington; Philip Warner, Sharon, all of Mass.

[73] Assignee: Northeastern University, Boston, Mass.

[21] Appl. No.: 263,929

[22] Filed: Jun. 21, 1994

[51] Int. Cl.⁶ ...................... C07C 233/00; C07C 235/00; C07C 221/00

[52] U.S. Cl. ...................... 546/268.1; 546/347; 564/169; 564/181; 564/188

[58] Field of Search ...................... 528/220, 229, 528/322; 546/347, 268.1; 564/188, 169, 181

[56] References Cited

U.S. PATENT DOCUMENTS

| | | | |
|---|---|---|---|
| 4,568,733 | 2/1986 | Parker et al. | 526/262 |
| 4,699,978 | 10/1987 | Barton | 536/27 |
| 4,721,669 | 1/1988 | Barton | 435/6 |
| 4,795,700 | 1/1989 | Dervan et al. | 435/5 |
| 4,837,312 | 6/1989 | Dervan et al. | 536/27 |
| 4,966,962 | 10/1990 | Sengupta | 530/317 |
| 4,980,473 | 12/1990 | Barton | 546/10 |
| 5,097,062 | 3/1992 | Nicolaou et al. | 560/231 |
| 5,112,974 | 5/1992 | Barton | 546/4 |
| 5,136,099 | 8/1992 | Skokotas et al. | 568/327 |
| 5,157,032 | 10/1992 | Barton | 514/185 |
| 5,180,818 | 1/1993 | Cech et al. | 536/23.1 |
| 5,183,942 | 2/1993 | Nicolaou et al. | 568/375 |
| 5,184,020 | 2/1993 | Hearst et al. | 250/455.11 |
| 5,225,556 | 7/1993 | Barton | 546/88 |
| 5,229,375 | 7/1993 | Maligres et al. | 514/75 |
| 5,239,118 | 8/1993 | Nicolaou et al. | 564/191 |
| 5,272,056 | 12/1993 | Burrows et al. | 435/6 |
| 5,276,159 | 1/1994 | Smith et al. | 548/147 |
| 5,281,710 | 1/1994 | Smith et al. | 546/18 |

OTHER PUBLICATIONS

"Photochemical Reagents Cleave Proteins Efficiently", C&EN, Sep. 5, 1994.
Bregant et al., "New Class of DNA–Cleaving Agents Based on Trimethylenemethane[1]", *J. Am. CHem. Soc.* 116:3635–3636, Apr. 20, 1994.
Dwyer et al., "Design and Binding of a Distamycin A Analog...", *J. Am. Chem. Soc.* 114:5912–5919, Jul., 1992.
Wade et al., "Design of Peptides that Bind in the Minor Groove of DNA...", *J. Am. Chem. Soc.* 114:8783–8794, Nov. 4, 1992.
Mrksich et al., "Antiparallel Side–by–Side Heterodimer for Sequence–Specific...", *J. Am. Chem. Soc.* 115:2572–2576, Apr. 7, 1993.
Mrksich et al., "Design of a Covalent Peptide Heterodimer...", *J. Am. Chem. Soc.* 116:3663–3664, Apr. 20, 1994.
He et al., "Microgonotropens and their Interactions with DNA...", *J. Am. Chem. Soc.* 116:3716–3725, May 4, 1994.
American Chemical Society–Division of Organic Chemistry, 207th ACS National Meeting, #337, Mar., 1994. Rugabalasooriar et al.
J. P. Behr, "Photohydrolysis of DNA by Polyaminobenzenediazonium Salts", *J. Chem. Soc. Chem. Commun.*, pp. 101–103, Jan., 1989.
Griffitsh et al., "Cleavage of DNA Resulting from Exposure to Phenyl Radicals", *J. Chem. Soc. Chem. Commun.*, pp. 24–26, Jan. 1, 1992.
Burckhardt et al., "Binding of Nonintercalative Antitumor Drugs to DNA–polymers:...", *J. of Biom. Struc. & Dynam.* 4:813–831, 1987.
Boger et al., "CDPI₃–Enediyne and CDPI₃–EDTA Conjugates:...", *J. Org. Chem.* 58:3018–3024, May 21, 1993.
Northeastern University 23rd American Chemical Society Regional Meeting, #178–179, Jun., 1993.
Arya et al., "Development of New DNA–Binding and Cleaving Molecules: ...", *Tetrahedron Letters* 34:7823–7826, Dec. 3, 1993.
Allinger, *Organic Chemistry*, (1971), Worth Publishers, p. 573.
Matsushita, CA 76:35052 (1971).
CA 113:191933, Rao et al. (1990).

*Primary Examiner*—Jeffrey Mullis
*Attorney, Agent, or Firm*—Weingarten, Schurgin, Gagnebin & Hayes LLP

[57] ABSTRACT

Reagents for cleaving or crosslinking of biomolecules using nondiffusible reactive intermediates and a method of using the reagents. In one embodiment, the DNA binding element includes a phenyl group on each end, and each terminal phenyl group contains at least one reactive group X:

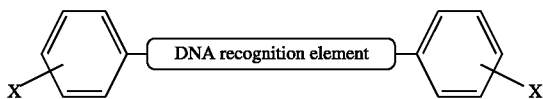

The reactive groups X may function to either cleave or crosslink the DNA to which the reagent is bound. Reactive groups that cleave the DNA include radical species formed by the decomposition of diazonium ions or the hydrolysis of azocarboxylates and cationic species formed, for example, by the photolysis of diazonium ions. Crosslinking moieties include nitrenes generated from the photolysis of azides.

12 Claims, 10 Drawing Sheets

REAGENTS FOR CLEAVAGE OR CROSSLINKING OF BIOMOLECULES USING NONDIFFUSIBLE REACTIVE INTERMEDIATES

FIELD OF THE INVENTION

This invention relates to reagents for the cleavage and/or crosslinking of nucleic acids, especially deoxyribonucleic acid (DNA), and more particularly to the cleavage and crosslinking of DNA by nondiffusible reactive intermediates.

BACKGROUND OF THE INVENTION

Molecules that cleave DNA have become indispensable tools in chemistry and biology. These molecules have facilitated the analysis of DNA structure and conformation, the study of DNA-protein interactions, and the implementation of strategies for DNA sequencing. More recently, these molecules have also been promoted as prosthetic groups for antisense oligonucleotides the site-selectively destroy a bound target sequence. In addition, DNA cleaving reagents are also potential antitumor drugs. Thus, there is great interest in the development of new molecules capable of sequence-specific DNA cleavage. The d(A-T) -specific, minor groove binding drug NSC-101327 (FIG. 1) has been shown to bind to duplex DNA, but does not cleave it. The central part of the drug is presumably involved in specific hydrogen bonding to dA.dT pairs.

DNA cleaving agents include restriction endonucleases. Restriction endonucleases are proteins which contain binding elements which recognize and cleave DNA at very specific sites within the DNA polymer. The sequence-specific cleavage of DNA has proven to be useful in a variety of analytic procedures including DNA sequence determination, chromosome analyses, and recombinant DNA manipulations. However, unless the DNA polymer contains the proper sequence of bases that are recognized by the endonuclease, cleavage will not occur. In addition, the limited number of known endonucleases, each specific for a respective nucleotide sequence, limits the number of potential cleavage sites.

While most restriction endonucleases require the target sequence to be double stranded, site specific cleavage of single-stranded DNAs has also been reported. U.S. Pat. No. 5,180,818 to Cech et al. discloses site specific cleavage of a single-stranded DNA by providing an RNA molecule having a deoxyribonuclease activity independent of any protein, and contacting that RNA molecule with the single stranded DNA molecule to cause the single stranded DNA molecule to be cleaved.

Chemical DNA cleaving reagents fall principally into three categories: hydrolytic agents, alkylators and radical generators. The nucleases, including the endonucleases just discussed, hydrolyze the phosphodiester backbone of DNA, belong to the first category. Almost all hydrolytic agents contain a metal ion at the active site that is believed to aid in the hydrolysis either by providing Lewis acidity or through the delivery of a coordinated nucleophile. Although the development of small, "artificial" hydrolytic agents has proven difficult, the binding of small molecules to DNA, both in the minor groove and via intercalation has been pursued. U.S. Pat. Nos. 4,699,978, 4,721,669, 4,980,473, 5,112,974, and 5,127,032 to Barton describe coordination complexes that result in the cleavage of DNA.

The alkylating agents of the second category attack the nucleic acid bases by forming covalent complexes. The resulting covalent complexes then lead to direct strand breaks or alkali labile abasic sites. Mitomycin C, nitrogen mustards and CC-1065 belong to this category of agents. Recently, simple molecules that are capable of DNA alkylation have also been developed. However, the fact that they have low alkylation efficiencies have hindered their wide spread application.

The third category of agents, the radical generators, generally target the deoxyribose moieties. Such generators can generate either diffusible or non-diffusible radicals to abstract hydrogen from the 1', 4' or 5' positions of the ribose ring. The subsequent reaction of the resulting DNA radicals with molecular oxygen leads to their destruction. For years, the generation of hydroxyl radicals in a metal catalyzed Haber-Weiss reaction has been the primary way to cleave DNA. Although elegant applications have been reported, the major limitation has been the "diffusible nature" of the oxidant (.OH) which usually leads to DNA strand scission at multiple sites, and the generation of asymmetric cleavage patterns.

U.S. Pat. No. 4,795,700 to Dervan et al. discloses that non-specific reagents which generate hydroxyl radicals or other, activated oxygen species could be effective agents to cleave biopolymers. These non-specific, diffusible radical sources are attached to specific binding reagents to cleave the molecule with some site specificity. Studies of non-diffusible oxidants using higher valent metal-oxo species are currently in their infancy.

An alternate approach to DNA cleavage uses "ene-diyne" natural products. The chemistry centers around the ability of ene-diyne moieties to generate non-diffusible, $sp^2$ carbon-centered biradicals via the Bergman cyclization. To date, virtually all attempts to generate non-diffusible carbon-centered biradicals have used only ene-diyne precursors. Although elegant, the syntheses of these ene-diynes are often challenging, and the bond-strain associated with these complex systems have caused some key synthetic steps to be low yielding.

U.S. Pat. Nos. 5,276,159 and 5,281,710 to Smith, U.S. Pat Nos. 5,097,062, 5,239,118, 5,237,101, 5,183,942 to Nicolaou et al., and U.S. Pat. No. 5,136,099 to Skokotas et al. describe the ene-diyne class of molecules with respect to their use as a DNA cleaving agent. The natural ene-diyne class of cleaving compound are effective due to their cyclization to diradical species subsequent to site-specific binding. The natural ene-diynes are complex molecules which are not easily modified with respect to their respective mechanism of cleavage. Attempts to tether simpler ene-diyne moieties to known DNA binding reagents such as distamycin or netropsin have not been particularly encouraging. Other diradical sources, such as trimethylenemethane precursors, are synthetically complicated and not highly modifiable. Both the ene-diyne class and trimethylenemethane precursors also suffer from lack of synthetic simplicity, generality, and flexibility.

SUMMARY OF THE INVENTION

The invention includes reagents for cleavage or crosslinking of biomolecules using nondiffusible reactive intermediates and a method of using the reagents. The reagents include a DNA binding element and at least one reactive group X. In one embodiment, the DNA binding element includes a phenyl group on each end, and at least one reactive group X as illustrated in FIG. 2.

The reactive groups X may function to either cleave or crosslink the DNA to which the reagent is bound depending on the type of reactive group present. Reactive groups that cleave the DNA include radical species formed from the decomposition of diazonium ions or the hydrolysis of azocarboxylates, and cationic species formed, for example, by the photolysis of diazonium ions. Crosslinking moieties include nitrenes generated from the photolysis of azides. As used herein, the term "biradical" refer to species where two radical centers are present at the same time The term "diradical" refers to species where two radical center may be formed sequentially, and need not be simultaneously present.

An important advantage of the disclosed compounds is the ability to convert didiazonium compounds to the corresponding bisazoesters which allows investigations of DNA cleavage under physiological conditions. Additionally, the didiazonium compounds may be converted to the corresponding diazides to function as interstrand cross-linking agents.

DESCRIPTION OF THE DRAWINGS

The invention will be more fully understood from the following detailed description taken in conjunction with the accompanying drawings in which.

DETAILED DESCRIPTION OF THE INVENTION

Figure 1:
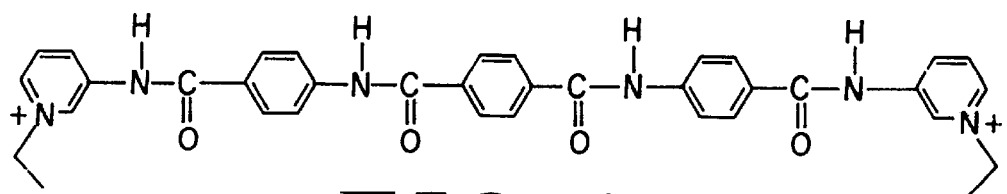
FIG. 1 is a diagram of a minor groove binding agent known to the prior art.
Figure 2:
FIG. 2 is a highly schematic diagram of an embodiment of the compound of the invention.

The invention includes reagents for cleaving or crosslinking nucleic acid biopolymers using nondiffusible reactive intermediates. The general structure of the reagents is shown in FIG. 2. Each reagent includes a DNA binding element and terminal phenyl groups that contain at least one reactive group X. The reactive groups X include cleaving and crosslinking moieties. Radicals formed by decomposition of diazonium ions, and the hydrolysis of azidocarboxylates act as cleaving agents as do cationic species formed by the photolysis of diazonium ions. Crosslinking moieties include nitrenes generated from the photolysis of azides. In one embodiment, compounds with two diazonium moieties attached to a DNA binding element, shown in FIG. 3, can deliver high concentrations of non-diffusible aryl diradicals along the strands of duplex DNAs. The interaction between the positively charged diazonium moieties and the negatively charged phosphodiester backbone can further increase the affinity of these molecules to DNA beyond the affinity provided by the DNA recognition element. In addition, the positive charges on the diazonium units render the molecule water-soluble. The recognition element may be designed to provide sequence-specificity and strong binding to DNA.

Although various structural entities may lend themselves to the construction of DNA binding molecules, the embodiments shown herein are based upon repeating benzene ring moieties, rather than derivatization of known DNA binding agents such as distamycin or netropsin with cleaving or cross-linking units. The syntheses disclosed herein are less laborius, cheaper, more versatile, and the resulting molecules more stable to a wide variety of conditions than binding molecules formed by the derivatization of known compounds. In addition, unlike the natural product cleavers, these compounds can cleave or cross-link DNA under a variety of conditions.

Figure 4:
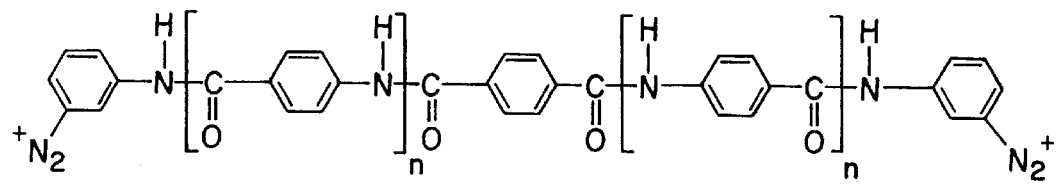
FIG. 4 is a diagram of an embodiment of the molecule of the invention.
Figure 5:
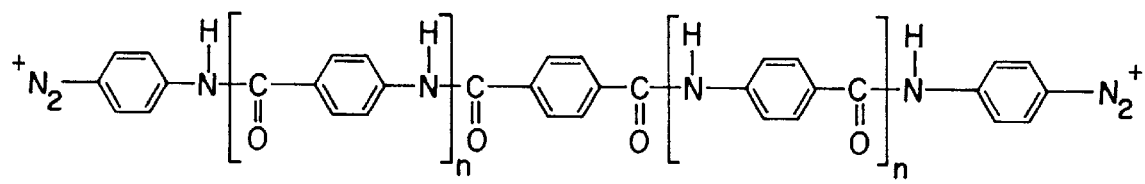
FIG. 5 is a diagram of another embodiment of the molecule of the invention.

In one embodiment, DNA cleaving reagents have the structure shown in FIGS. 4 and 5. FIG. 4 illustrates one embodiment of the invention wherein the cleaving moieties $N_2^+$ is oriented meta with respect to the NHCO group. FIG. 5 illustrates another embodiment of the invention wherein the cleaving moieties are oriented para with respect to the NHCO group. As described below, each of these embodiments are synthesized in similar steps, but with different starting reagents. In each embodiment, n is either 0 or 1.

Figure 6:
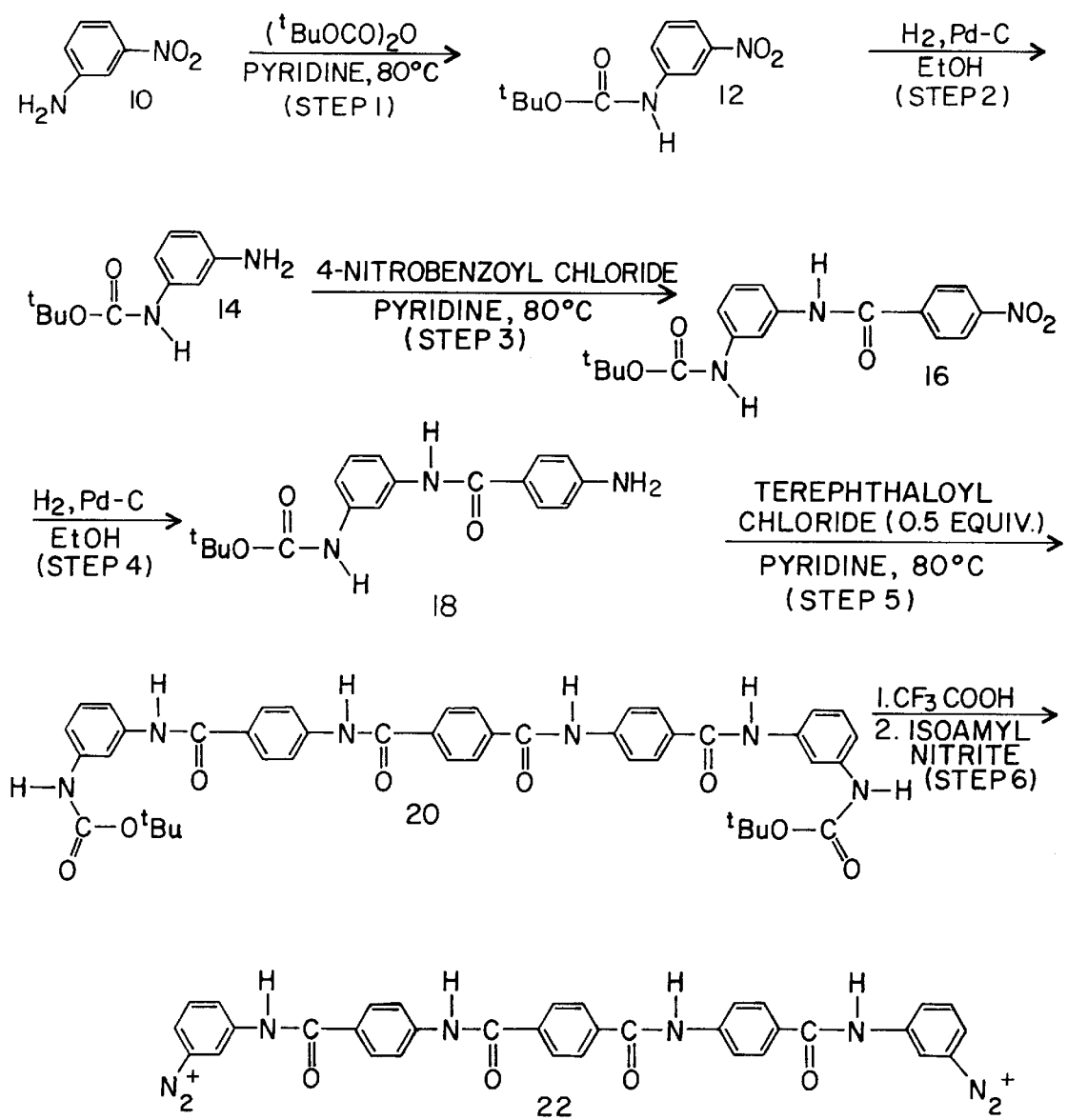
FIG. 6 is a diagram of an embodiment of a synthetic pathway of the embodiment of the invention shown in FIG. 4.

The synthesis of the structure shown in FIG. 4 is outlined FIG. 6. The amine function of commercially available 3-nitroaniline, 10 is protected with the tert-butyloxycarbonyl (BOC) group in the presence of pyridine at 80° C. (step 1) and the resulting compound, 12, is hydrogenated (3 atm. $H_2$, 10% Pd/C) (step 2) to obtain N-t-butoxycarbonyl-m-phenylenediamine, 14 (85%). This intermediate, on treatment with 4-nitrobenzoyl chloride (95%), again in the presence of pyridine at 80° C. (step 3) formed intermediate 16. This intermediate was hydrogenated as before (80%) (step 4) yielding N-t-butoxycarbonyl-p-aminobenzc,yl-m-phenylenediamine, 18. Heating 18 with 0.5 equivalents of terephthaloyl chloride in pyridine (step 5) afforded an N-protected cleaving agent, 20, of FIG. 3. Deprotection in the presence of $CF_3COOH$ and $CH_2Cl_2$ at room temperature followed by diazotization with isoamyl nitrite in acetic acid (step 6), yields the reactive product, 22. Starting with 4-nitroaniline and following the same synthesis, the product of FIG. 5 may be produced. In each case, the BOC-protecting group is important to obtain high yields and to facilitate isolation of pure products.

Figure 7:
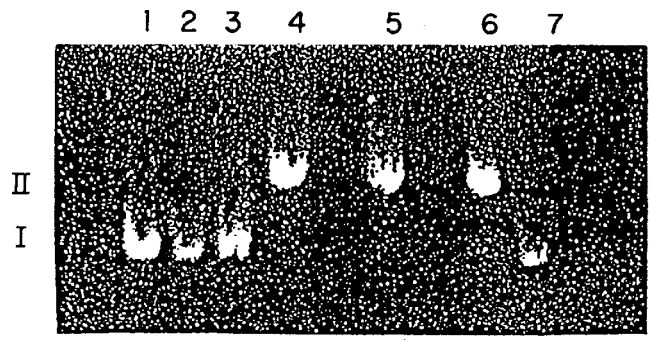
FIG. 7 is a diagram of an electrophoretic gel of DNA cleaved using the embodiment of the compound of FIG. 4.

The ability of the reagent of FIG. 4 to cleave the supercoile (Form I) DNA of the phage ΦI74 in the presence of $Cu^+$ and light is shown in FIG. 7. Each reaction mixture contains 0.25 ng of ΦX174 supercoiled DNA (14 nM) in 40 mM Tris-acetate (pH 8.2) containing 1 mM of EDTA. Unless indicated, all DNA cleavage reactions are run for 1 h at 25° C., and electrophoresis is conducted at 50V (3.0 h) a 0.7% agarose gel (dimension: 7×7 cm) in the presence of ethidium bromide. The content of each gel lane of FIG. 7 is as follows: lane 1, control ΦX174 DNA; lane 2, DNA+CuCl (3 μM); lane 3, DNA +the compound of FIG. 4 (1 μM); lane 4, DNA+CuCl (3 μM)+the compound of FIG. 4 (1 μM); lane 5, DNA+CuCl (0.3 μM)+the compound of FIG. 4 (0.1 μM); lane 6, DNA+hv+the compound of FIG. 4 (0.1 μM), 1 min.; lane 7, DNA+CuCl (3 μM)+the compound of FIG. 4 (1 μM)+distamycin A (100 μM). Form I—supercoiled DNA, Form II—relaxed DNA (single-strand cleavage).

Further, using such controlled experiments as (a) DNA+ the compound of FIG. 4 + CuCl, (b) DNA + the compound of FIG. 4, (c) DNA + CuCl, (d) DNA alone, and (e) DNA + the compound of FIG. 4 + CuCl + distamycin A, DNA cleavage occurs only when the cleaving reagent and cuprous chloride are present. In addition, photolysis of the reagent of FIG. 4 (254 nm, 1–2 min.) leads to DNA cleavage (lane 6).

The reagent of FIG. 4 exhibits much higher potency as a DNA cleaving agent than the ene-diyne mimics reported to date. That is, the Form I band of a solution containing 0.25 μg ΦX174 supercoiled DNA (14 nM) disappears completely in the presence of 0.1 μM 20 m and 0.3 μM cuprous chloride or light, whereas simple ene-diynes require much higher concentrations (500–1000 μM) to produce similar results. For example, under essentially identical conditions, 0.2 μM bleomycin was reported to produce cleavage of only 42% of the DNA. Thus, the disclosed reagents are more effective cleaving agents than bleomycin.

It is also found that the addition of distamycin A, a d(A·T)-specific minor groove binder, suppresses the DNA cleavage (lane 7). This suggests that the cleaving reagent is most likely binding to the minor groove of DNA, and that this binding may be contributing to the effectiveness of DNA cleavage.

Figure 8:
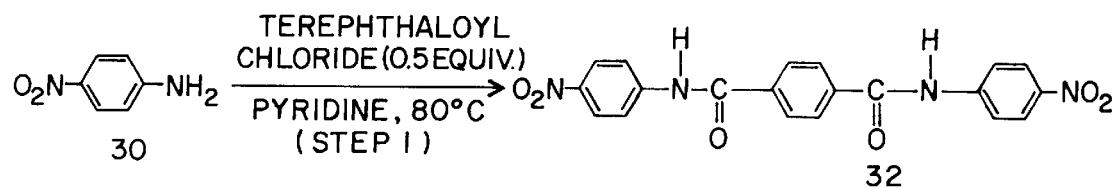
FIG. 8 is a diagram of an embodiment of a synthetic pathway of another embodiment of the invention.
Figure 8:
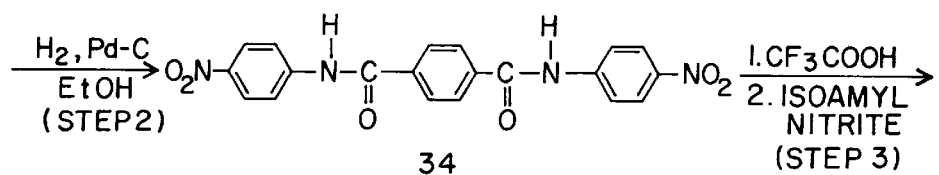
Figure 8:
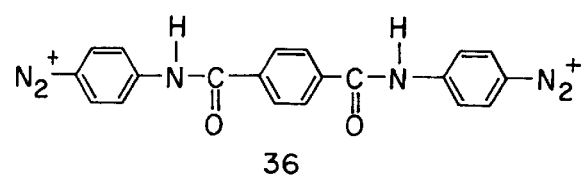

A homolog of the compound shown in FIG. 5 wherein n=0 is synthesized following the route outlined in FIG. 8. 4-Nitroaniline, 30, is treated with terephthaloyl chloride in pyridine at 80° C. (step 1). to produce terephthaloyl-bis-p-nitroanilide, 32. This intermediate, 32, is hydrogenated under pressure with a Pd/C catalyst in the presence of ethanol (step 4) and the resulting compound 34 is activated with trifluoroacetic acid and isoamyl nitrite (step 6) to give the activated product, 36.

Figure 9:
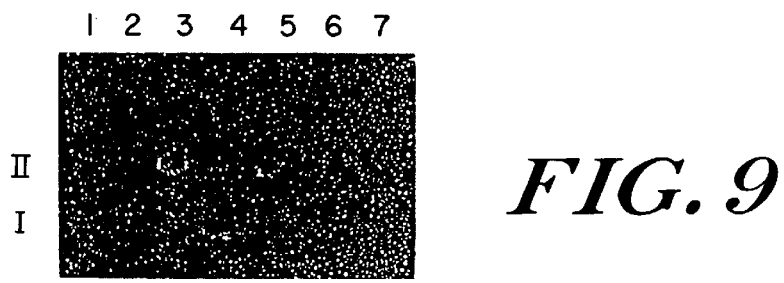
FIG. 9 is a diagram of and electrophoretic gel of DNA cleaved using the embodiment of the product of the synthesis of FIG. 8.

FIG. 9 illustrates cleavage of ΦX174 supercoiled DNA by the homologue synthesized in the reaction of FIG. 8. Each solution contained 0.25 ng of ΦX174 supercoiled DNA (14 nM) in 40 mM Tris-acetate, pH=8.2 containing 1 mM of EDTA. Unless indicated, all DNA cleavage reactions are run for 1 h at 25° C., and electrophoresis is conducted at 50V (3.0 h) on a 0.7 % agarose gel (dimension: 7×7 cm) in the presence of ethidium bromide. The content of each gel lane is as follows: lane 1, control ΦX174 DNA; lane 2, DNA+ $Fe^{2+}$ (0.2 μM) +activated product 36 (0.1 μM); lane 3, DNA+NaI (0.2 μM); lane 4, DNA+CuCl (0.2 μM)+activated product 36 (0.1 μM); lane 5, DNA+activated product 36 (0.1 μM)+hv (1 min.). Form I—supercoiled DNA, Form II—relaxed DNA (single-strand cleavage)

Highly reactive aryl dications are thought to be generated, from didiazonium salts (e.g., the structure of FIG. 3), under the photolytic condition used for the cleavage of DNA. Like any other electrophilic species, these may attack the nucleic acid bases which may lead to DNA strand breaks.

Figure 10:
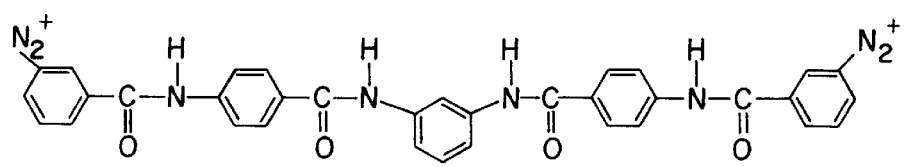
FIG. 10 is a diagram of a structure of an another embodiment of the invention.
Figure 11:
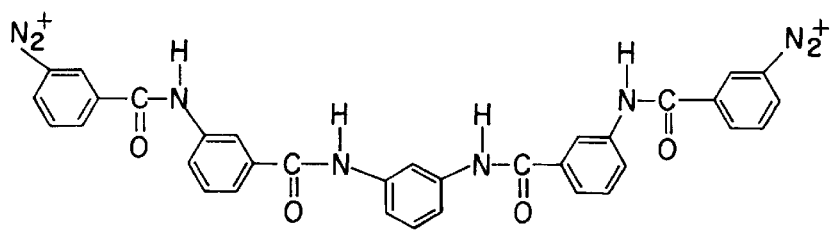
FIG. 11 is a diagram of a structure of another embodiment of the invention.
Figure 12:
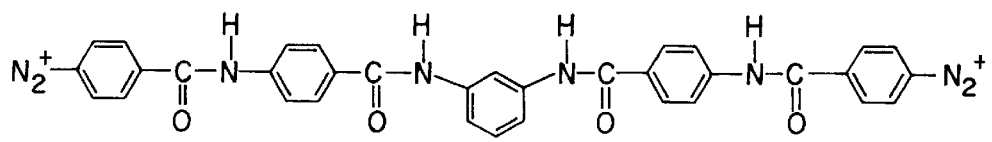
FIG. 12 is a diagram of a structure of another embodiment of the invention.
Figure 13:
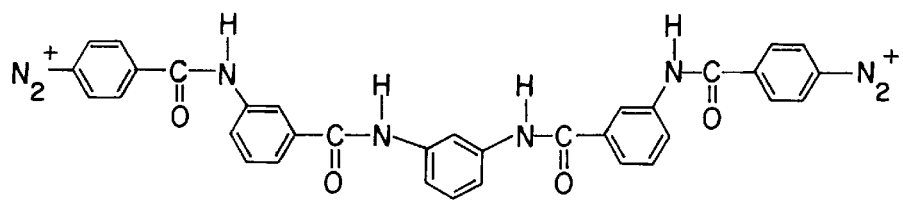
FIG. 13 is a diagram of a structure of another embodiment of the invention.

FIGS. 10, 11, 12, and 13 illustrate embodiments of the invention in which the central ring of each of these compounds is a meta-phenylenediamine. FIGS. 10 and 12 illustrate embodiments of the compound wherein the second and fourth phenyl rings contain substituents in a para arrangement. FIGS. 11 and 13 illustrate embodiments wherein the second and fourth phenyl rings are in a meta arrangement. In FIGS. 10 and 11, the $N_2^+$ group is oriented in the meta position on the terminal phenyl groups, and in FIGS. 12 and 13, the $N_2^+$ group is oriented in the para position. The meta arrangement on the central phenyl ring is necessary to properly orient the binding NH groups to the duplex DNA and contrast to the terephthalic acid (para) nature of the central ring of FIG. 3. Computer modeling studies indicate a high spatial correlation of the meta-phenylenediamine ring to the central ring of distamycin (which has an aminopyrrolecarboxamide structure). This correlation can be attributed to the change in bond angles engendered by switching from a 6-ring in the former to a 5-ring in the latter.

The compounds of FIGS. 10–13 are useful to define the be geometry for the binding and the concurrent interaction of the diazonium groups with the phosphodiester backbone of the DNA. When the latter interaction is maximized, the aryl dications (generated from didiazonium salts under photolytic conditions) alkylate the phosphodiester backbone. Thus, proper design and selection of method for activation of our diazonium salts create opportunities to cleave DNA by three different procedures: diradical-attach-on-sugar, dication-alkylation-on-nucleic-acid-bases, or dication-phosphodiester-alkylation approach.

Figure 14:
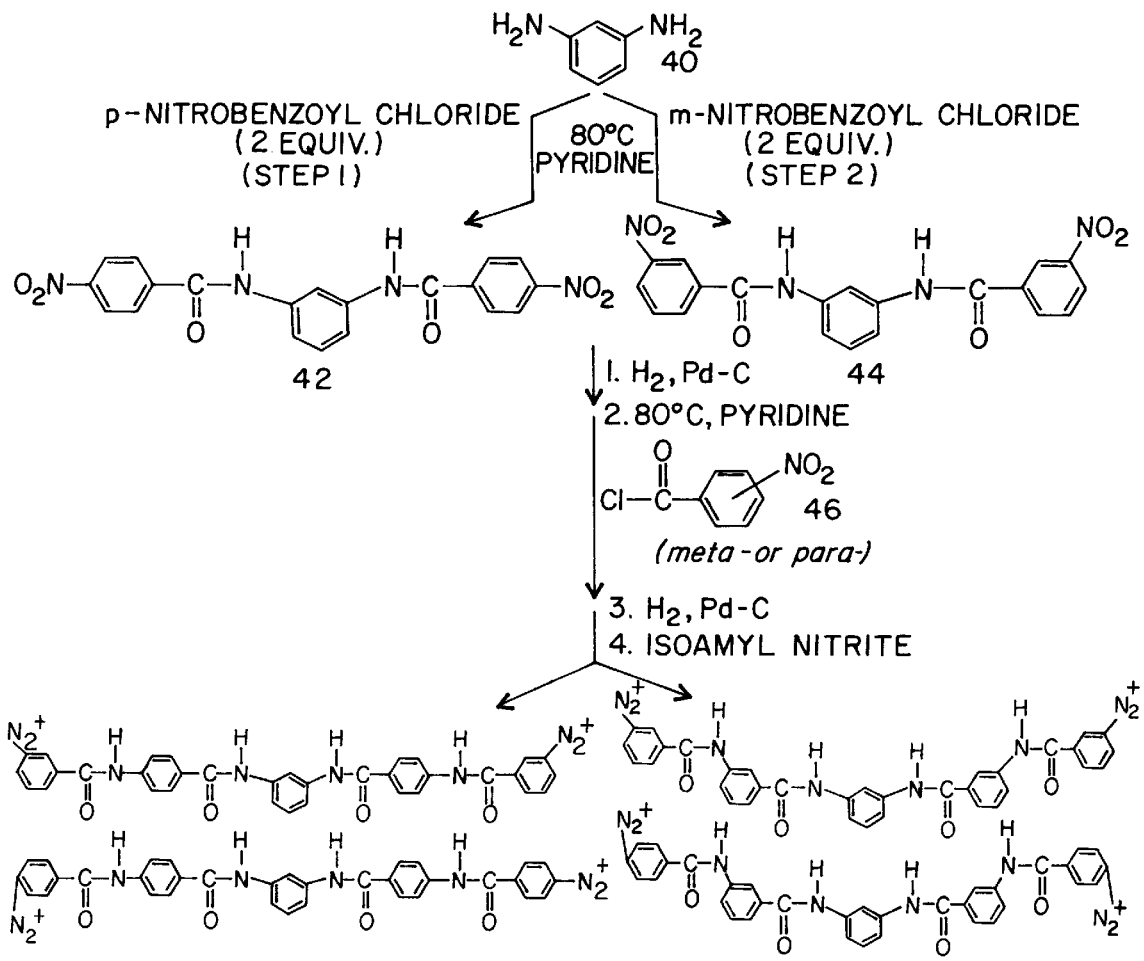
FIG. 14 is a diagram of an embodiment of a synthetic pathway for synthesizing the compounds of FIGS. 10–13.

The syntheses of the structures shown in FIGS. 10–13 are illustrated in FIG. 14. m-Phenylendiamine 40 is treated with either 2 equivalents of p-nitrobenzoyl chloride (step 1) or m-nitrobenzoyl chloride (step 2) in pyridine to give products with a nitro group oriented para, 42, or meta, 44, respectively to the NHCO group. Each of these intermediates is then hydrogenated in the presence of hydrogen and a hydrogenation catalyst (step 3) and subsequently reacted with meta- or para- nitrobenzoyl chloride 46 (step 4). The products are again hydrogenated (step 5) and activated with isoamyl nitrite (step 6) to yield the compounds of FIGS. 10 and 12, or FIGS. 11 and 13.

Figure 3:
FIG. 3 is a diagram of an embodiment of a compound of the molecule of the invention.
Figure 15:
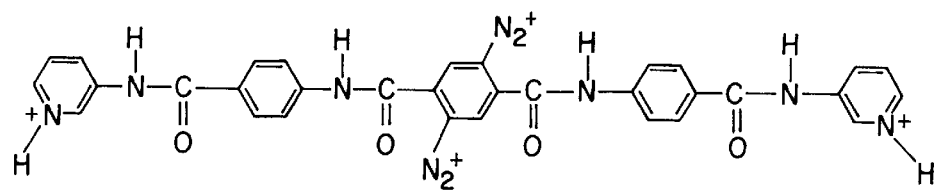
FIG. 15 is a diagram of another embodiment of the invention.
Figure 16:
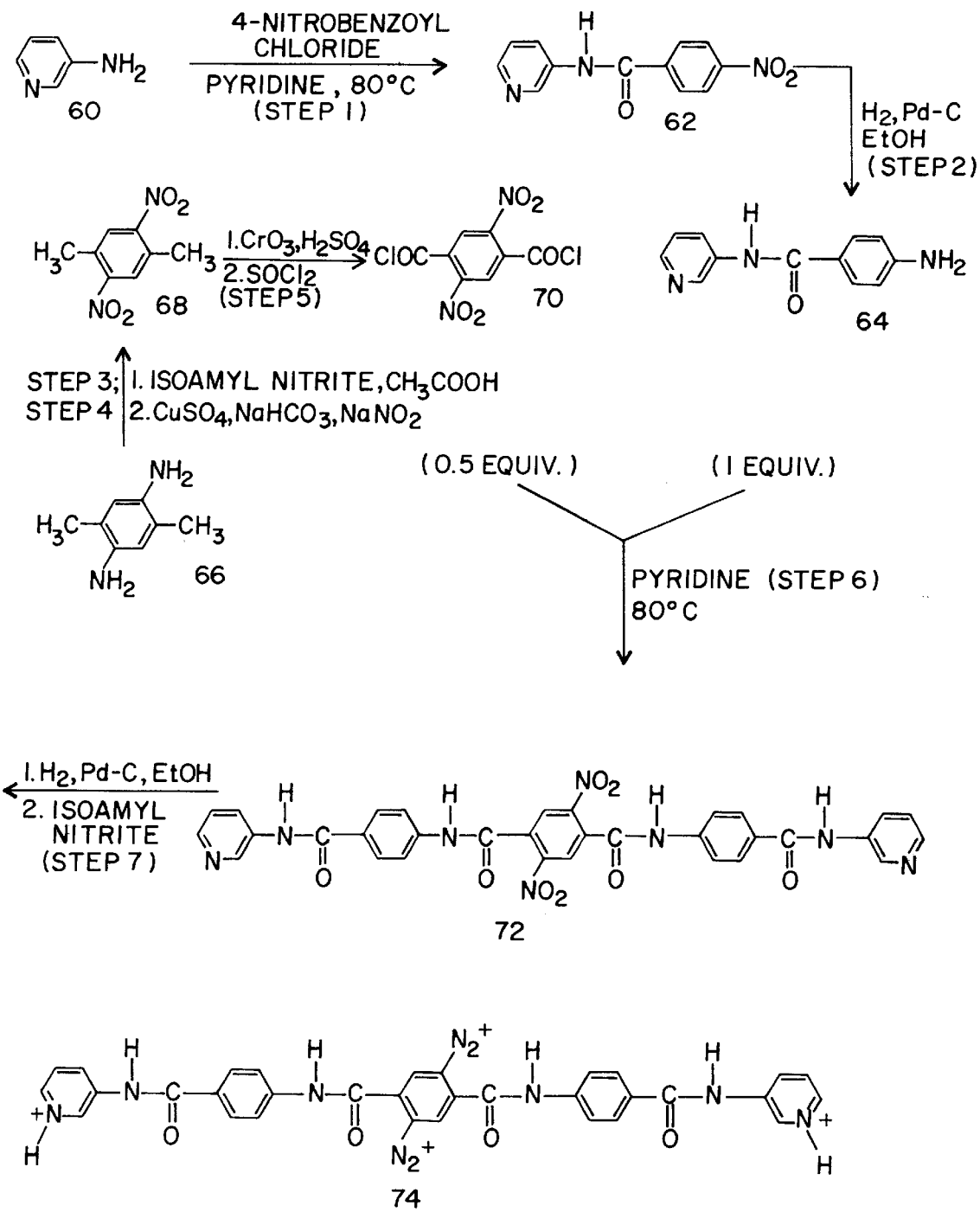
FIG. 16 is a diagram of an embodiment of a synthetic pathway for the embodiment of the compound of FIG. 15.

In an alternative embodiment, the diradical centers may be located on the central phenyl ring as illustrated in FIG. 15. 1,4-diradical type precursors (i.e., wherein the radical-generating functions are oriented para with respect to each other on the central phenyl ring) may be designed to include the minor groove binding features of NSC-101327, distamycin, or the structure of FIG. 3, or they may be built to mimic the minor groove intercalative ability of the ene-diyne antibiotic dynemicin. The compound illustrated in FIG. 15. is an example of a 1,4-diradical generator. The synthesis of this structure is shown in FIG. 16

3-Aminopyridine, 60, is first reacted with 4-nitrobenzoyl chloride in the presence of pyridine at 80° C. (step 1) and the product, 62, is subsequently hydrogenated in the presence of ethanol (step 2) to give N-(p-aminobezoyl)-3-aminopyridine, 64. In a separate reaction, 2,5-dimethyl-1,4-phenylenediamine, 66, is converted to 2,5-dimethyl-1,4-dinitrobenzene in a "reverse" Sandmeyer reaction with isoamyl nitrite and acetic acid (step 3), and subsequently treated with copper sulfate in the presence of sodium nitrite (step 4) to produce the intermediate, 68. This intermediate, 68, is oxidized with $CrO_3$ and chlorinated with $SOCl_2$ (step 5) to give 2,5-dinitroterephthaloyl chloride 70. One equivalent of N-(p-aminobezoyl)-3-aminopyridine, 64, and 0.5 equivalent of 2,5-dinitroterephthaloyl chloride, 70, are reacted in pyridine (step 6) to produce a bis-anilide derivative of 2,5-dinitroterephthaloyl chloride 72, and the product is again hydrogenated and activated with isoamyl nitrite (step 7) to yield the final activated product 74.

The related 1,3-biradicals (FIG. 17) are also be effective cleavers of DNA. The compound of FIG. 17 is prepared from 2,5-dimethyl-1,3-phenylenediamine, 66, and 3-nitropyridine, 60, as shown in FIG. 16.

Figure 17:
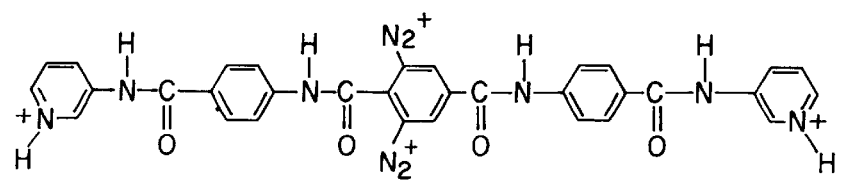
FIG. 17 is a diagram of another embodiment of the invention.
Figure 18:
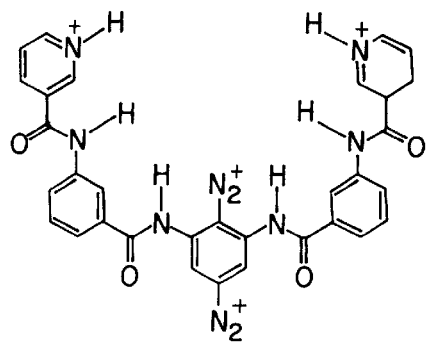
FIG. 18 is a diagram of another embodiment of the invention.
Figure 19:
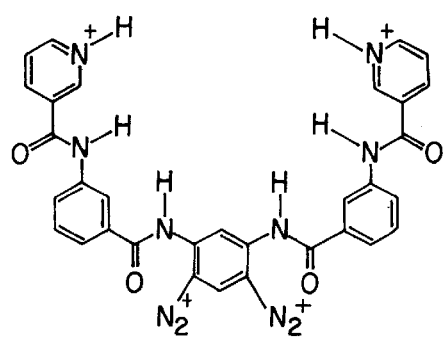
FIG. 19 is a diagram of another alternative embodiment of the invention.
Figure 20:
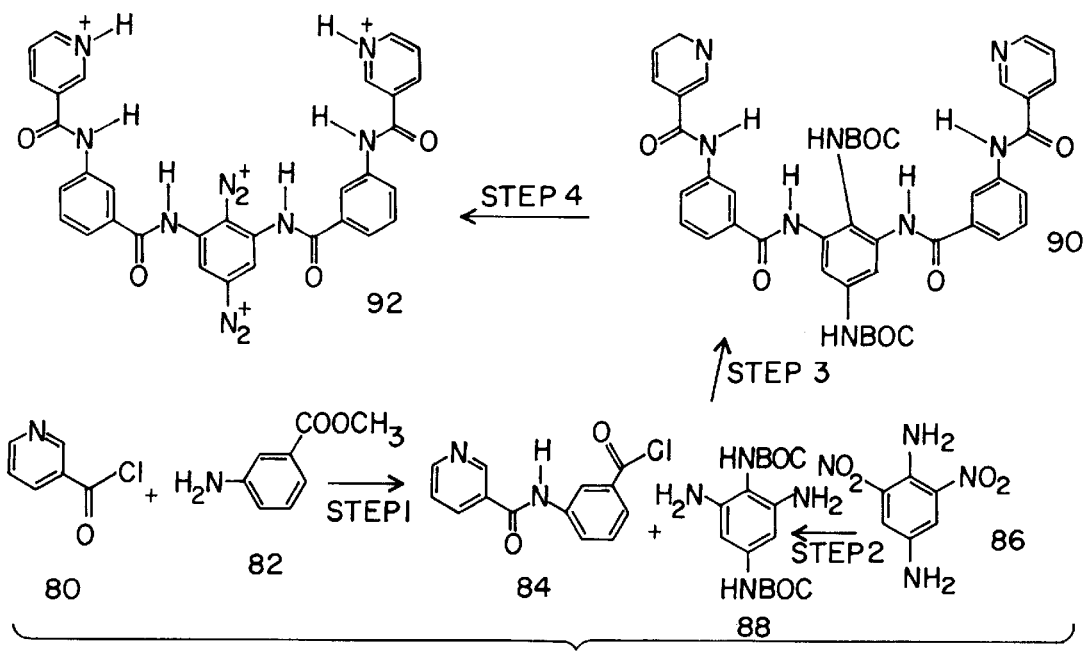
FIG. 20 is a diagram of an embodiment of a synthetic pathway for the compound of FIG. 18.
Figure 21:
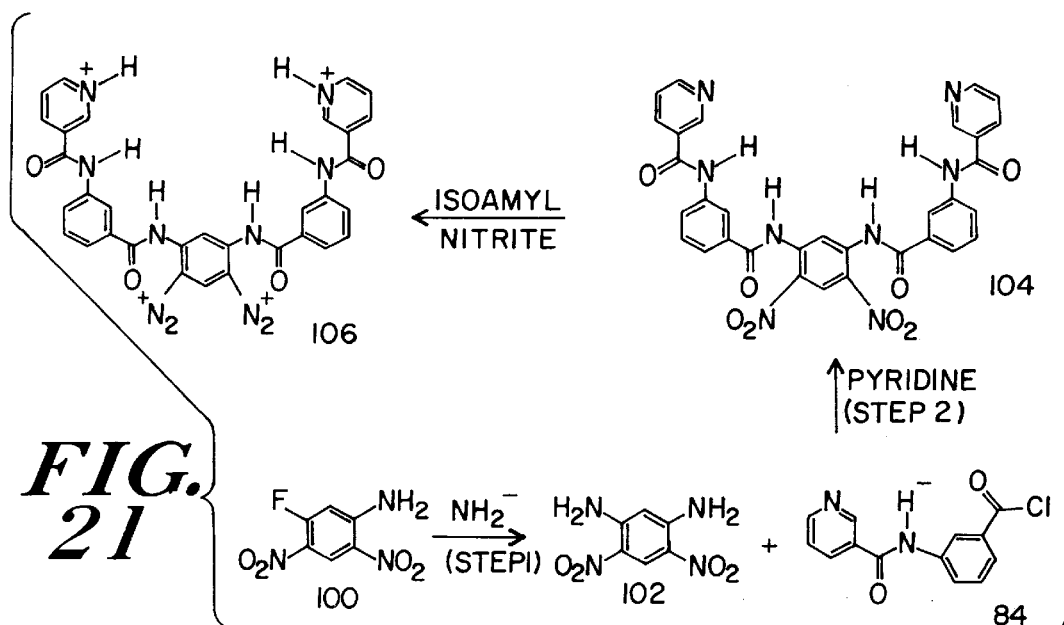
FIG. 21 is a diagram of an embodiment of a synthetic pathway for the compound of FIG. 19.

In some situations, the para-substituted arrangement of the central phenyl ring of the structures of FIGS. 15 and 17 may not be ideal for binding to DNA. Rather, a meta-substitution pattern would be preferable, as illustrated in the compounds of FIG. 18 and 19. The compound of FIG. 18 may be produced according to the reaction scheme set forth in FIG. 20. 3-Pyridylcarbonyl chloride, 80, is reacted with m-aminoethylbenzoate, 82, to give, after hydrolysis and treatment with $SOCl_2$, N-(m-phenylchlorocarbonyl)-3-pyridylcarboxamide, 84. In a separate reaction, 2,6-dinitro-1,4-phenylenediamine 86 is reacted with t-BOC and reduced to produce 88. 88 and 84 are reacted in pyridine to produce 90, which is treated with trifluoroacetic acid and isoamyl nitrite to yield the activated product 92.

The compound of FIG. 19 may be made from commercially available Bergmann's reagent 100. Bergmann's reagent 100 is treated $NH_2^-$ to afford 102, and upon reaction with 84 yields 104. 104 is subsequently reduced and treated with isoamyl nitrite to produce the activated product 106.

Although any DNA cleaving molecule may be considered as a potential anticancer drug, an important requirement is that its generation and/or activation be compatible with physiological conditions. The conditions commonly employed for the generation of aryl diazonium salts (from aryl amines), however, are not physiological. In addition, the need to use light or Cu(I) for activation makes didiazonium reagents less attractive for in vivo applications.

Figure 22:
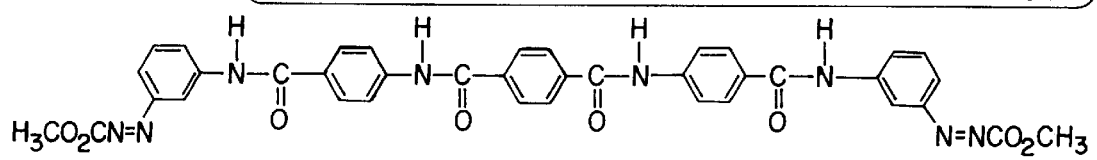
FIG. 22 is another embodiment of a compound of the invention.
Figure 24:
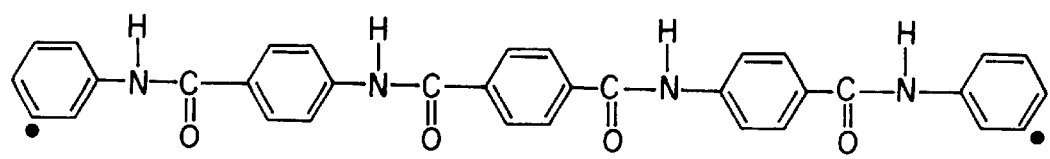
FIG. 24 is a diagram of the activated compound produced from the embodiment of the invention shown in FIG. 23.

Azoesters are another class of precursors for aryl diradicals that offer the advantage of nucleic acid cleavage under physiological conditions. An example of an azoester is the structure shown in FIG. 22. In neutral or slightly basic aqueous solutions, this compound undergoes hydrolysis and decarboxylation to produce an unstable bisdiazene which, in the presence of oxygen, decomposes to generate a DNA-cleaving radical, or the biradical shown in FIG. 24.

Figure 23:
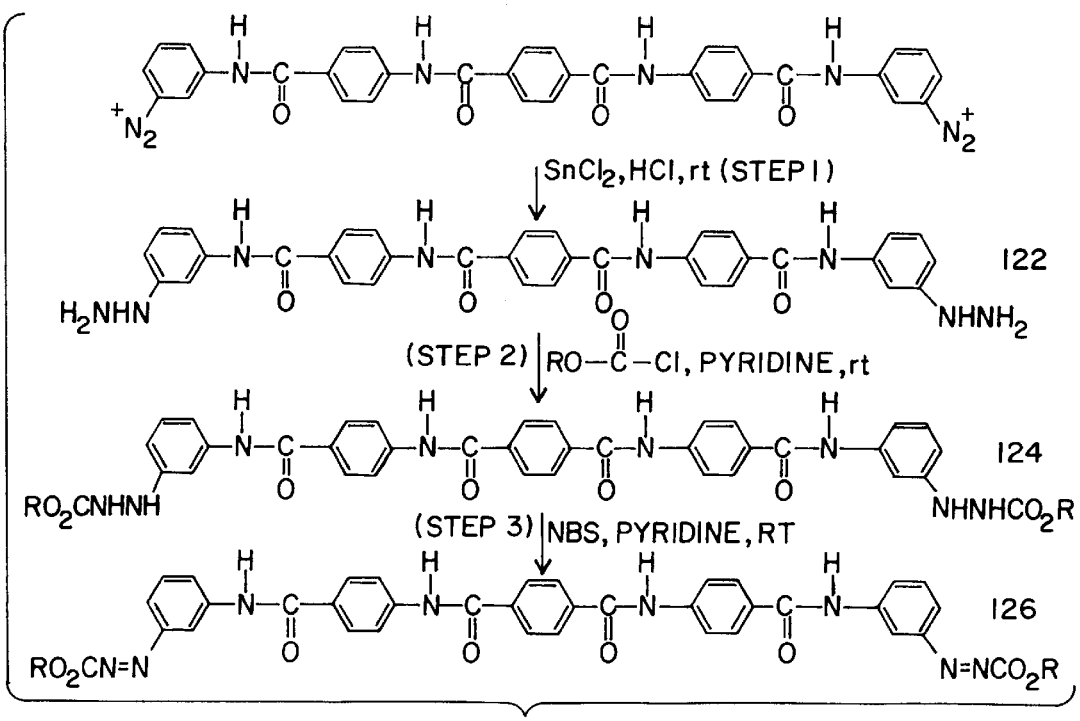
FIG. 23 is a diagram of an embodiment of synthetic pathway of another embodiment of the invention.

As illustrated in FIG. 23, azoester derivatives may be synthesized starting with the compound of FIG. 3. This compound is reduced with $SnCl_2$ and HCl (step 1) to give the product 122. This intermediate is then acylated in pyridine with an acylating agent that adds a carboxylate group and includes an R function (step 2) to prouduce 124. The R group includes groups such as $CH_3$, $K^+$, $CH_2(CH_2)_mN^+Me_3$ (M=1–5), Ar, $CH_2CH_2SO_2Ar$, $(CH_2)_pCO_2$-succinyl (P=1–5), or the like. Oxidation of 124 with N-bromosuccinimide in pyridine affords the stable compound 126 (step 3).

Figure 25:
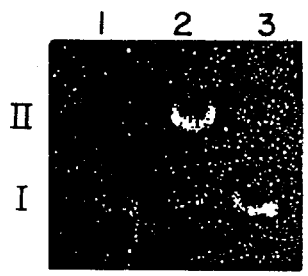
FIG. 25 is a diagram of an electrophoretic gel of DNA cleaved with the compound of FIG. 23.

FIG. 25 shows cleavage of ΦX174 supercoiled DNA by the bisazoester produced by the scheme of FIG. 23. All cleavage reactions are run about 12 hours at 25° C. Electrophoresis is conducted at 50V (3.0 h) on a 0.7agarose gel (7×7 cm) and is stained with ethidium bromide. The buffers are 40 mM Tris-acetate, 1 mM EDTA (pH 8.2). Lane 1 is control ΦX174 DNA (0.25 μg,14 nM) in the buffer; lane 2 is DNA (0.25 μg, 14 nM)+product 126 wherein R=$CH_3$ in a 1:1 buffer and THF mixture; lane 3 is DNA (0.25 μg,14 nM)+product 126 wherein R=$CH_3$ in the buffer.

The bisazoester is less soluble in aqueous buffers, and DNA cleavage is insignificant unless it is dissolved in tetrahydrofuran and mixed with a buffer containing the DNA (lane 2 versus lane 3). Other didiazonium compounds are also similarly converted to the corresponding azoesters and have the ability to cleave DNA.

Figure 26:
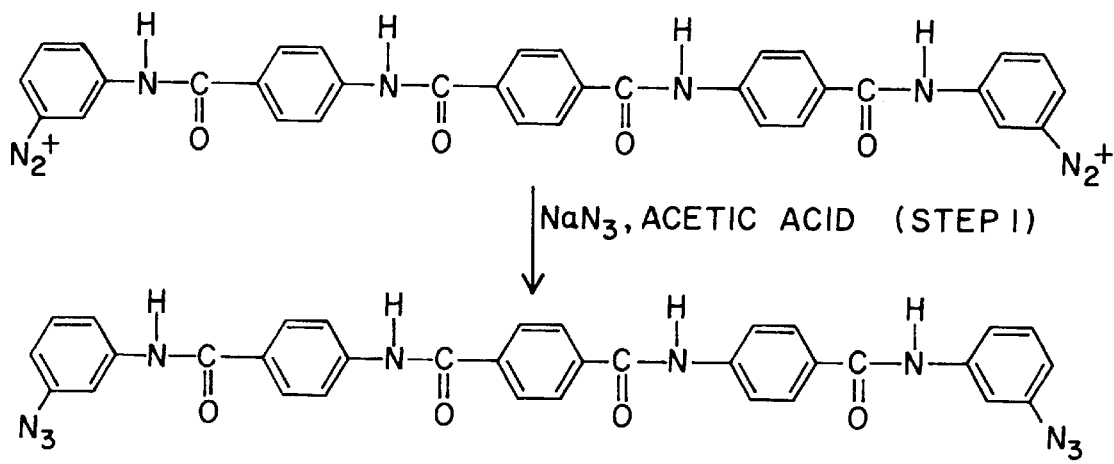
FIG. 26 is a diagram of an embodiment of a synthetic pathway for another embodiment of the invention.

As illustrated in FIG. 26, aryl diazides may also be synthesized from the compounds of the invention. Unlike the diazonium compounds, the azides have the advantage of chemical stability prior to photolysis. When irradiated, however, such molecules will insert into biological macromolecules and form a stable covalent bond. Therefore, photolysis in the presence of DNA leads to permanent enzymatically irreparable crosslinking.

Figure 27:
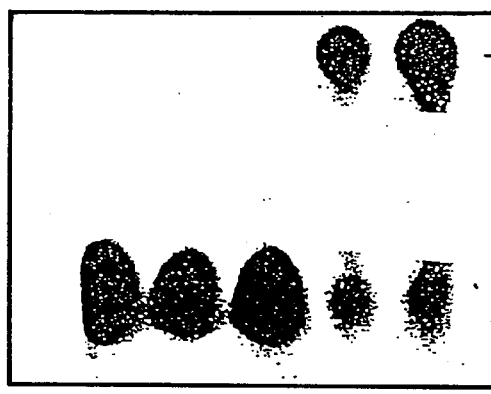
FIG. 27 is a diagram of an electrophoretic gel of DNA crosslinked with the compound produced by the synthesis of FIG. 26.

As illustrated in FIG. 26, the compound of FIG. 3 may be converted to the corresponding diazide upon reaction with sodium azide in the presence of acetic acid at room temperature (step 1) to yield a product with azido group oriented meta to the respective CONH group 130. Photolysis of this compound in the presence of an oligonucleotide duplex d (5'-CGCGATTGCGC) d(5'-GCGCAATCGCG) produces the photolyzed products which are analyzed by gel electrophoresis. FIG. 27 illustrates interstrand crosslinking of oligonucleotide duplex d(5'-CGCGATTGCGC).d(5'-GCGCAATCGCG) by the diazide produced in FIG. 25. The oligonucleotide duplex is formed by annealing the [5'-$^{32}$P] end labeled d(5'-CGCGATTGCGC) (1 μg, 0.025 μM) with its complementary, unlableled strand d(5'-GCGCAATCGCG) in a pH=7.8 buffer containing 20 mM Tris acetate, 1 mM EDTA, and 50 mM NaCl. Denaturing PAGE (20%) is performed at 450V. Lane 1 is labeled oligonucleotide; lane 2 is labeled oligonucleotide exposed to UV light (254 nm, 1–2 min); lane 3 is labeled oligonucleotide plus diazide (40 μM) in the dark; lane 4 is labeled oligonuclecotide plus diazide (40 μM) exposed to room (visible) light for 12 h; lane 5 is labeled oligonucleotide plus diazide (40 μM) exposed to UV light (254 nm, 1–2 min).

As shown in FIG. 27, the slower migrating band on the denaturing polyacrylamide gel electrophoresis indicates that crosslinking occurs between the duplex strands of DNA. In addition, as indicated by lanes 4 and 5, light and the diazide are both needed for crosslinking.

Figure 28:
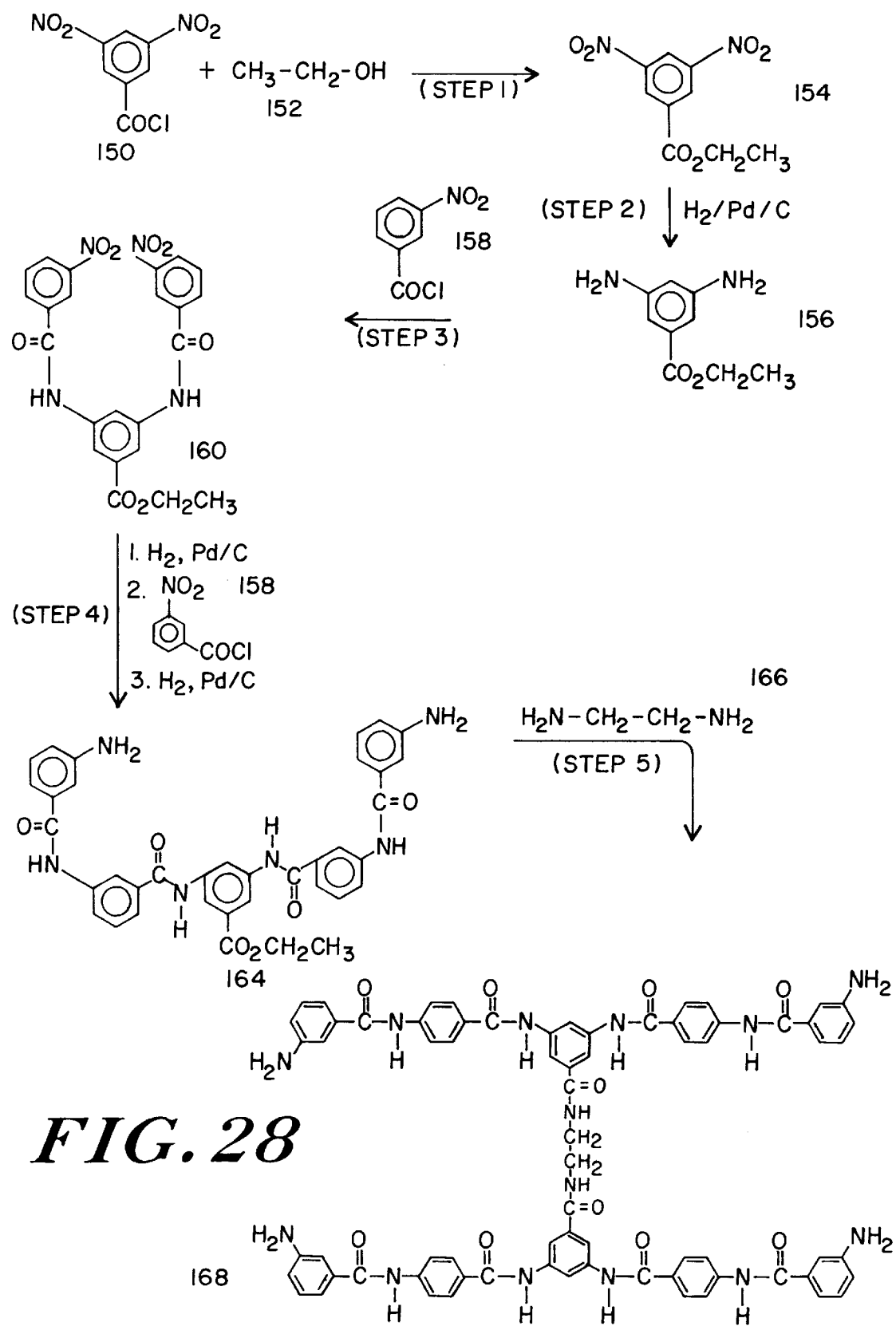
FIG. 28 is a diagram of an embodiment of a synthetic pathway for another embodiment of the invention.

As illustrated in FIG. 28, dimeric forms of the compounds may also be produced. In one embodiment, 3,5-dinitrobenzoyl chloride, 150 is reacted with ethanol 152 (step 1) to produce the carboxyethyl derivative intermediate 154. Intermediate 154, in turn, may be converted to the diamino structure, 156, with hydrogen in the presence of a suitable hydrogenation catalyst (step 2). Reaction with m-nitrobenzoyl chloride, 158, gives the corresponding meta compound (step 3), which is again hydrogenated and treated with m-nitrobenzoyl chloride (step 4) to produce, after reduction with hydrogen in the presence of a catalyst, the compound of 164. The intermediate product 164 is then reacted with ethylenediamine 166 (step 5) to produce the dimer compound 168.

Although the invention has been shown and described with respect to an illustrative embodiment thereof, it should be appreciated that the foregoing and various other changes, omissions and additions in the form and detail thereof may be made without departing from the spirit and scope of the invention as delineated in the claims.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 11 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: YES ( i v ) ANTI-SENSE: NO ( x i ) SEQUENCE DESCRIPTION: SEQ ID NO:1:

C G C G A T T G C G   C                                                                                                                                  1 1

We claim:
1. A compound of the formula

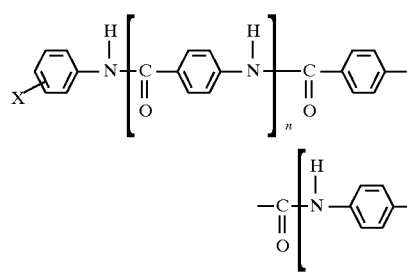

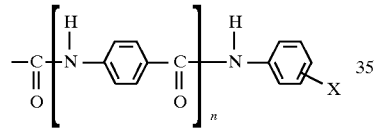

wherein
n=0 or 1;
$X=N_2^+$, $N_3$, $N{=}N{-}CO_2R$;
  wherein $R=CH_3$, $K^+$, $CH_2(CH_2)_mN^+(CH_3)_3$, Ar, $CH_2CH_2SO_2Ar$, or $(CH_2)_pCO_2$-succinyl, m =1 –5, p=1–5;
at least one X being present; and
X being oriented either meta or para with respect to the NH group.

2. A precursor of the formula

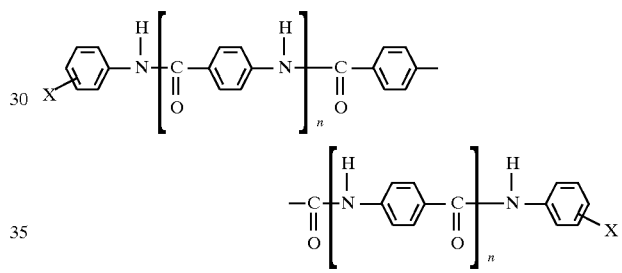

wherein
n=0 or 1;
$X = NH_2$;
at least one X being present; and
X being oriented either meta or para with respect to the NH group.

3. A compound of the formula

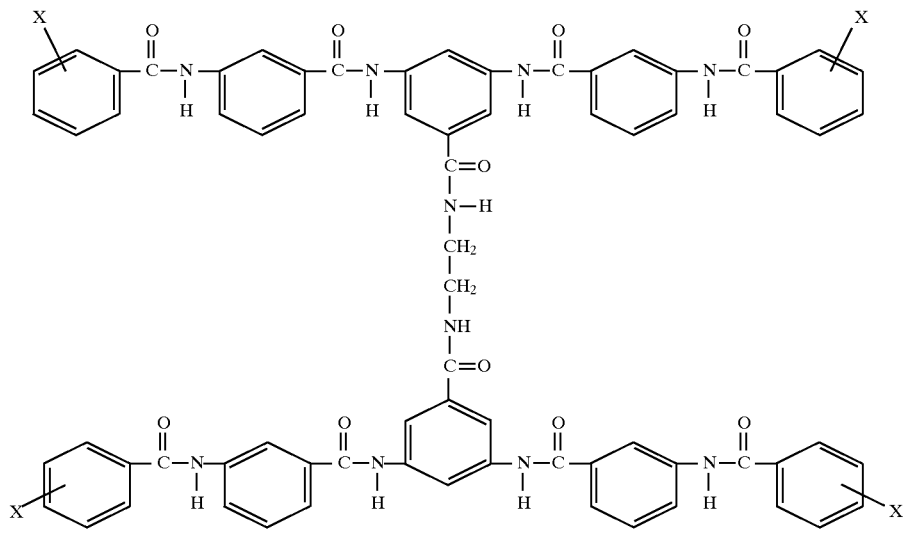

wherein $X = N_2^+$, $N_3$, $N=N-CO_2R$;
 wherein $R = CH_3$, $K^+$, $CH_2(CH_2)_m N^+(CH_3)_3$, Ar, $CH_2CH_2SO_2Ar$, or $(CH_2)_p CO_2$-succinyl, $m=1-5$, $p=1-5$;

at least two X being present; and

X being oriented either meta or para with respect to the CO group.

4. A precursor of the formula

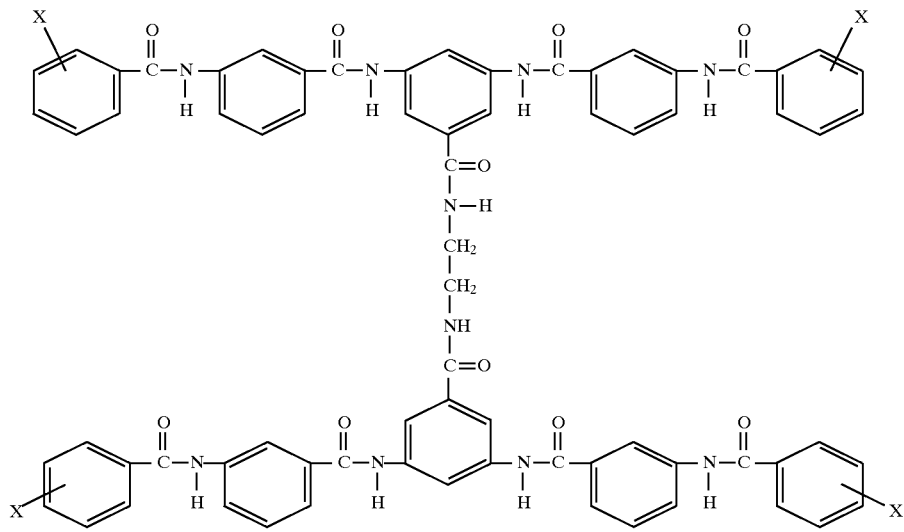

wherein $X = NH_2$;

at least two X being present; and

X being oriented either meta or para with respect to the CO group.

5. A compound of the formula

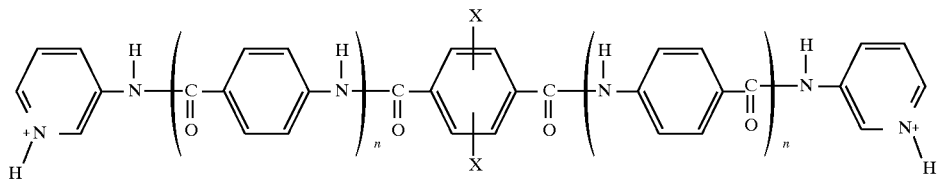

wherein
  n=0 or 1;
  X=$N_2^+$, N=N—$CO_2$R;
    wherein R=$CH_3$, $K^+$, $CH_2(CH_2)_m N^+(CH_3)_3$, Ar, $CH_2CH_2SO_2$Ar, or $(CH_2)_p CO_2$-succinyl, m=1–5, p=1–5;
  at least two X being present.

6. A precursor of the formula

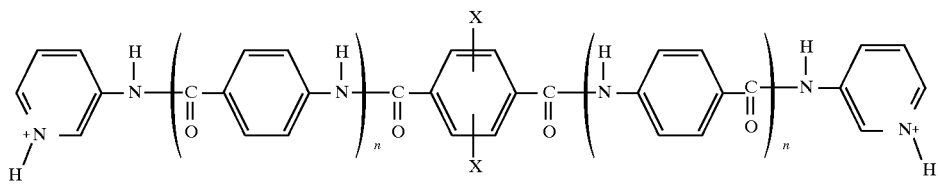

wherein
  n=0 or 1;
  X=$NH_2$;
  at least two X being present.

7. A compound of the formula

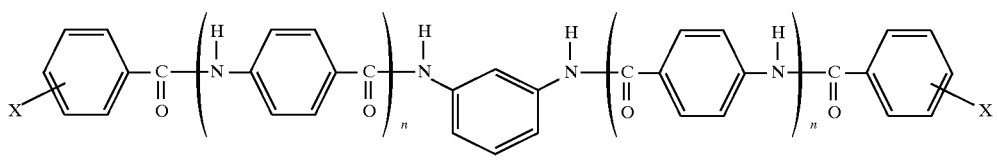

wherein
  n=0 or 1;
  X=$N_2^+$, $N_3$, N=N—$CO_2$R;
    wherein R=$CH_3$, $K^+$, $CH_2(CH_2)_m N^+(CH_3)_3$, Ar, $CH_2CH_2SO_2$Ar, or $(CH_2)_p CO_2$-succinyl, m=1–5, p=1–5;
  at least one X being present; and
  X being oriented either meta or para with respect to the CO group.

8. A precursor of the formula

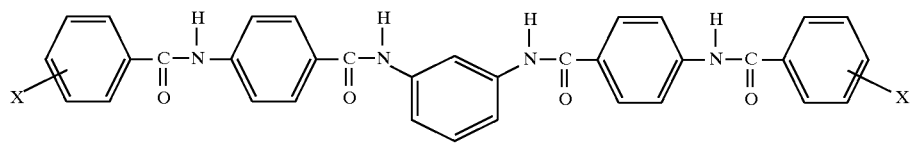

wherein
X=NH$_2$, one X being present on each terminal phenyl ring, and X being oriented either meta or para with respect to the CO group.

9. A compound of the formula

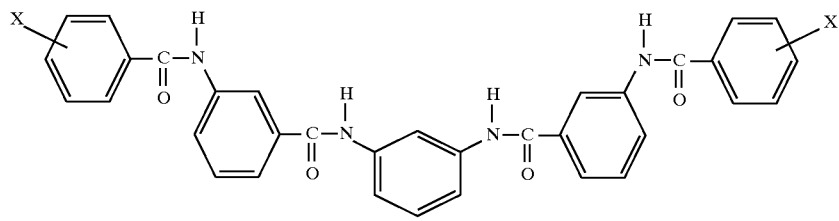

wherein
X=N$_2^+$, N$_3$, N=N—CO$_2$R;
wherein R=CH$_3$, K$^+$, CH$_2$(CH$_2$)$_m$N$^+$(CH$_3$)$_3$, Ar, CH$_2$CH$_2$SO$_2$ Ar, or (CH$_2$)$_p$CO$_2$-succinyl, m=1–5, p=1–5;
at least one X being present; and
X being oriented either meta or para with respect to the CO group.

10. A precursor of the formula

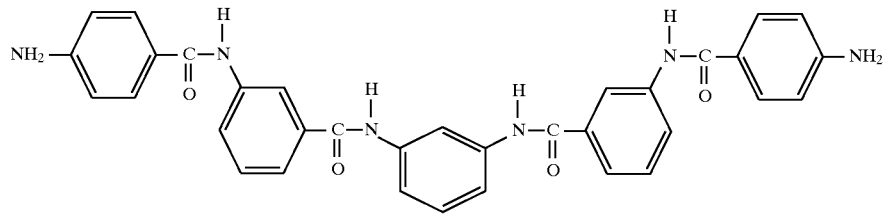

11. A compound of the formula

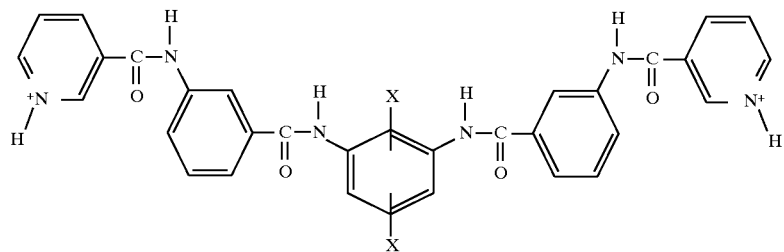
wherein
  $X = N_2^+$, $N{=}N-CO_2R$;
  wherein $R = CH_3$, $K^+$, $CH_2(CH_3)_m N^+(CH_3)_3$, Ar, $CH_2CH_2SO_2Ar$, or $(CH_2)_p CO_2$-succinyl, $m = 1-5$, $p = 1-5$;
  at least two X being present.
12. A precursor of the formula
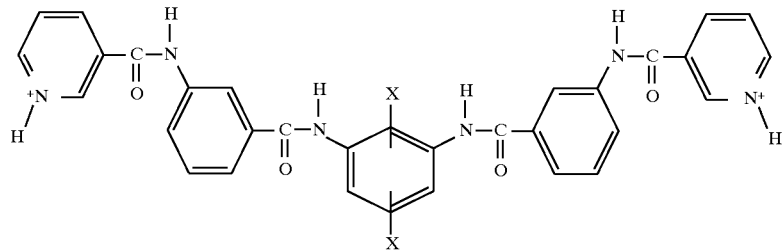
wherein
  $X = NH_2$;
  at least two X being present.
* * * * *

UNITED STATES PATENT AND TRADEMARK OFFICE
CERTIFICATE OF CORRECTION

PATENT NO.   : 5,770,736
DATED        : June 23, 1998
INVENTOR(S)  : Dev P. Arya et al.

It is certified that error appears in the above-identified patent and that said Letters Patent is hereby corrected as shown below:

Column 1,
Line 20, reads "the" should read -- to --.
Line 29, reads "dA.dT" should read -- dA•dT --.

Column 2,
Line 18, reads "(.OH)" should read -- (•OH) --.

Column 5,
Line 6, reads "aminobenzc,yl" should read -- aminobenzoyl --.
Lines 17-18, reads "supercoile" should read -- supercoiled --.

Column 6,
Line 34, reads "be" should read -- best --.

Column 8,
Line 1, reads "0.7agarose" should read -- 0.7% agarose --.

Column 9,
Lines 30-35, all four square brackets in formula should be parenthesis.

Column 10,
Lines 30-35, all four square brackets in formula should be parenthesis.

UNITED STATES PATENT AND TRADEMARK OFFICE
CERTIFICATE OF CORRECTION

PATENT NO.     : 5,770,736
DATED          : June 23, 1998
INVENTOR(S)    : Dev P. Arya et al.

It is certified that error appears in the above-identified patent and that said Letters Patent is hereby corrected as shown below:

<u>Column 17,</u>
Line 17, formula reads "$CH_2(CH_3)_mN^+(CH_3)_3$," should read -- $CH_2(CH_2)_mN^+(CH_3)_3$, --

Signed and Sealed this

Twenty-first Day of August, 2001

*Attest:*

*Nicholas P. Godici*

NICHOLAS P. GODICI
*Attesting Officer*     *Acting Director of the United States Patent and Trademark Office*